(12) United States Patent
Wang

(10) Patent No.: US 11,517,006 B2
(45) Date of Patent: Dec. 6, 2022

(54) METHOD FOR REUSING CONDENSATE FORMED ON A GRILL OF AN INSECT REPELLENT DEVICE

(71) Applicant: Thermacell Repellents, Inc., Bedford, MA (US)

(72) Inventor: Wender Wang, Bedford, MA (US)

(73) Assignee: Thermacell Repellents, Inc., Bedford, MA (US)

( * ) Notice: Subject to any disclaimer, the term of this patent is extended or adjusted under 35 U.S.C. 154(b) by 37 days.

(21) Appl. No.: 16/749,276

(22) Filed: Jan. 22, 2020

(65) Prior Publication Data

US 2021/0235684 A1  Aug. 5, 2021

Related U.S. Application Data

(63) Continuation of application No. 15/658,938, filed on Jul. 25, 2017, now abandoned.

(60) Provisional application No. 62/366,876, filed on Jul. 26, 2016.

(51) Int. Cl.
*A01M 1/20* (2006.01)
*A01M 29/12* (2011.01)
*A61L 9/03* (2006.01)

(52) U.S. Cl.
CPC .......... *A01M 1/2061* (2013.01); *A01M 29/12* (2013.01); *A61L 9/03* (2013.01); *A01M 2200/01* (2013.01)

(58) Field of Classification Search
CPC .............. A01M 1/2022; A01M 1/2061; A01M 1/2088; A01M 29/12; A01M 2200/01

USPC .................................................... 43/129, 130
See application file for complete search history.

(56) References Cited

U.S. PATENT DOCUMENTS

| | | | |
|---|---|---|---|
| 2009/0196587 A1* | 8/2009 | Cheung ..................... | A61L 9/14 392/394 |
| 2015/0060565 A1* | 3/2015 | Furner ...................... | A61L 9/12 239/34 |
| 2015/0342172 A1* | 12/2015 | Sharma ............... | A01M 1/2088 43/124 |

FOREIGN PATENT DOCUMENTS

| FR | 2929685 A1 * | 10/2009 | .......... A01M 1/2088 |
|---|---|---|---|
| WO | WO-2011142918 A1 * | 11/2011 | ............. A01N 25/26 |

OTHER PUBLICATIONS

FR 2929685 A1, European Patent Office Machine translation, original French language patent in Non-final Office Action dated Jun. 17, 2021.

* cited by examiner

*Primary Examiner* — Peter M Poon
*Assistant Examiner* — Kari A Bradberry
(74) *Attorney, Agent, or Firm* — MacMillan, Sobanski & Todd, LLC

(57) ABSTRACT

An operating device creating a rising heated vapor which passes through a grill having a concave surface enabling the condensate formed on the grill to migrate towards the center of the grill and away from the periphery of the grill which prevents condensate from dropping onto the operating device interfering with its operation.

6 Claims, 7 Drawing Sheets

METHOD FOR REUSING CONDENSATE FORMED ON A GRILL OF AN INSECT REPELLENT DEVICE

RELATED APPLICATIONS

This patent application incorporates the contents of parent patent application Ser. No. 15/658,938, filed Jul. 25, 2017 and claims the priority of provisional patent application Ser. No. 62/366,876, filed Jul. 26, 2016, the contents of which are incorporated herein.

BACKGROUND OF THE INVENTION

This invention relates to redirecting condensate formed in an operating device generating heat and a rising vapor and a grill thereabove which allows the vapor to pass therethrough but generates condensation thereon due to the temperature difference between the heat generating device and the vapor as compared to the grill. The grill has a lower center than its outside perimeter, and the condensate migrates toward the center, thereby dropping thereon being reheated and reused.

A preferred embodiment of this invention comprises a heating plate, a mat or pad carrying a liquid ingredient and a grill thereabove where the mat is heated to evaporate the liquid ingredient to form the rising vapor which causes condensate to form on the grill.

Prior art grills generally have a convex shape formed of ribs through which the evaporated liquid or rising vapor passes. Some passes therethrough, and condensate forms mostly on the surface of the ribs facing the heating plate. This condensate drips onto the outer portions or periphery of the device causing potential damage. The grill is provided to keep the user's fingers away from the heating plate.

An object of this invention is to provide a grill for redirecting captured condensate toward the center of the grill and dripping the condensate on the heat generating device to re-evaporate the condensate. Thus, the condensate does not drip into the device in the area of its periphery.

Another object of this invention is to provide such a grill with a concave shape toward the center of the grill so that the center of the grill is slightly lower than the outer periphery of the grill, thereby directing the condensate to drip towards the center of the grill, onto the heating plate which re-evaporates the condensate.

The grill can have different shapes to fit on top of the operating device.

Other objects, advantages and features of this invention will become more apparent from the following description.

SUMMARY OF THE INVENTION

This invention relates to an operating device which provides heat to evaporate a liquid which passes through a grill. Some of the evaporated vapor passes through the grill and some is retained as condensate on the grill.

In a specific embodiment of this invention, an insect repellent device having a heating plate on which a mat sits with active insect repellent ingredient saturated therein is provided. The active ingredient is evaporated, forming a vapor to provide an insect free zone. These devices have a grill located above the plate. In accordance with this invention, the grill has downwardly biased or concave ribs, allowing condensate formed on the ribs to drip onto the heating plate below the grill. Normally, the condensate on a convex grill migrates to the outer edges of the grill because the center of the grill is slightly higher than the periphery. The condensate drips onto the unit in the area of its periphery as the condensate migrates. By providing a concave cross-sectional shape for the grill, such that the center of the grill is below the outer edges, the condensate will tend to migrate towards the center of the grill and, as it does, it drips from the ribs directly onto the heating plate and pad carried thereon. Therefore, the condensate will be reused and re-evaporated so that there is a saving of condensate, and further, dripping of condensate onto the working elements of the unit is minimized.

BRIEF DESCRIPTION OF THE PHOTOGRAPHS/DRAWINGS

DETAILED DESCRIPTION

Figure 1:
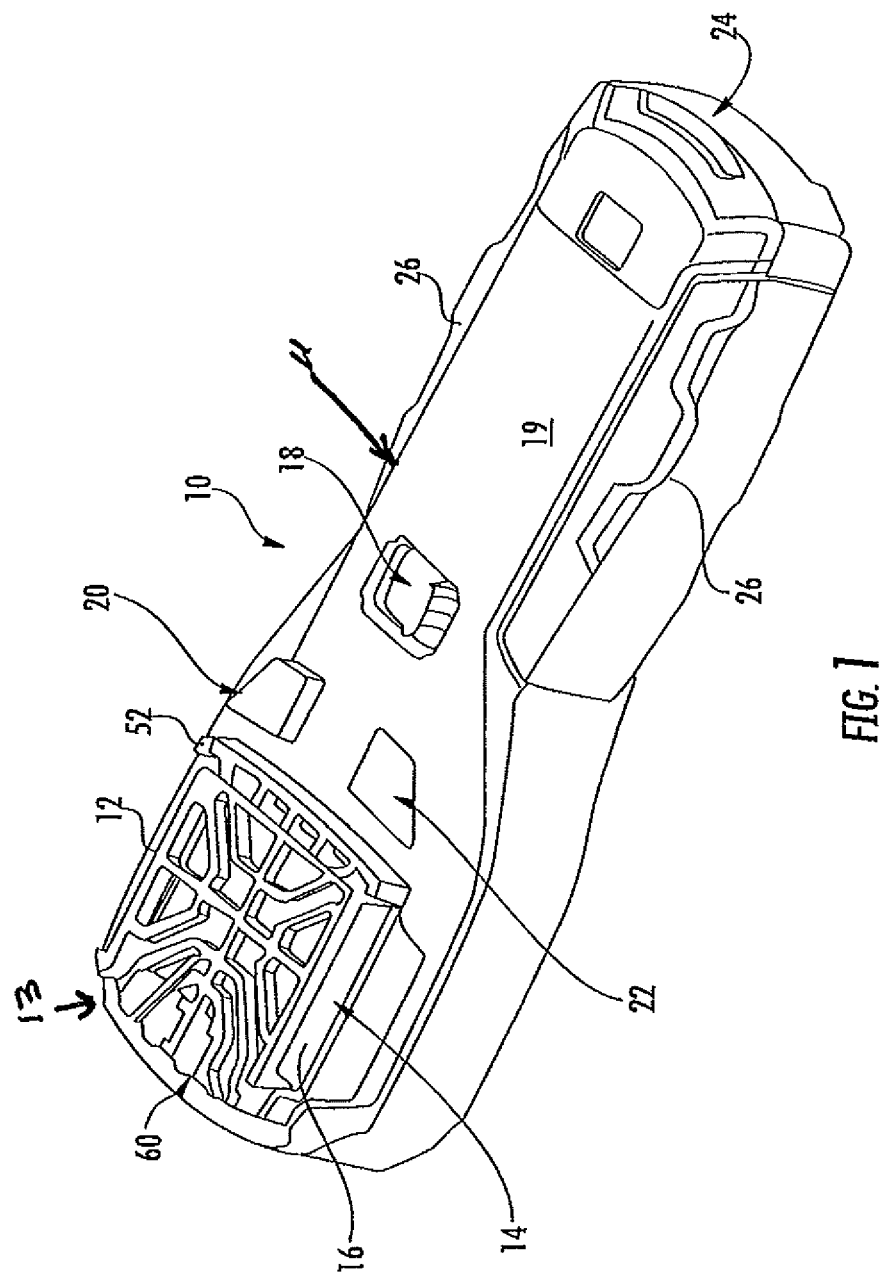
FIG. 1 is a top perspective view of an embodiment of this invention.

FIG. 1 is a top perspective view of an illustrative embodiment of this invention, which is an insect repellent device 10 having a grill 12 located above a heating plate 14 on which a mat 16 carrying an active liquid ingredient is located.

The device is the subject of prior U.S. Pat. No. 5,700,430 (hereinafter '430), the contents of which are incorporated herein. The device 10 has a body 11 and an insect repellent section 13.

The illustrative embodiment of this invention is directed to an insect repellent device. This invention is directed to an operating device generating heat to produce a heated vapor which passes through a grill in which some of the heated vapor passes through the grill and some forms a condensate on the grill. This invention is directed to providing a grill shape which causes the condensate to migrate inward from the periphery of the grill, dropping on the operating device so as to be reheated and rise as a vapor through the grill. Additionally, by causing condensate to move inwardly and be reheated, the condensate will not drip on the device below.

When the device 10 is to be operated, and as described in the '430 patent directed to an insect repellent device, a fuel on/off switch 18 located in the center of lower body 19 is switched to the ON position, and a valve for an internal butane cartridge is opened, allowing butane fuel to flow. Ignition button 20 is depressed, igniting a flame to heat heater plate 14. Indicator light 22 connected to sense when fuel is flowing is lit, indicating that the device is working. The indicator light 22 is powered by a conventional coin-shaped battery and will turn OFF when the device is turned off or fuel stops flowing. Indicator light 22 allows the user to determine the state of operation of the unit without having to examine the device to see if a flame exists.

While light indicator 22 may indicate the current state of operation of device 10, that light 22 or additional indicator lights viewable on device 10 may be used to indicate that the state being displayed is that the device is warming up or that the heater plate temperature dropped below the level needed to volatilize the active ingredient. These are additional states in which the temperature of the plate 14 is sensed, and depending on its temperature and preset parameters, certain states are reached, and display light 22 or additional display lights indicate the condition sensed. Additionally, light indicator 22 or another light indicator can be used to display that the heating plate temperature is sufficient to be volatilizing the active ingredient.

Cartridge end cap 24 is capable of being pulled out from or pushed into the bottom of the repellent device 10 in order to allow butane cartridges to be replaced if the device is powered by butane.

For ease of handling, rubber grips 26 on body 19 are located on either side of the body 11, which is to be held by the user.

Figure 2:
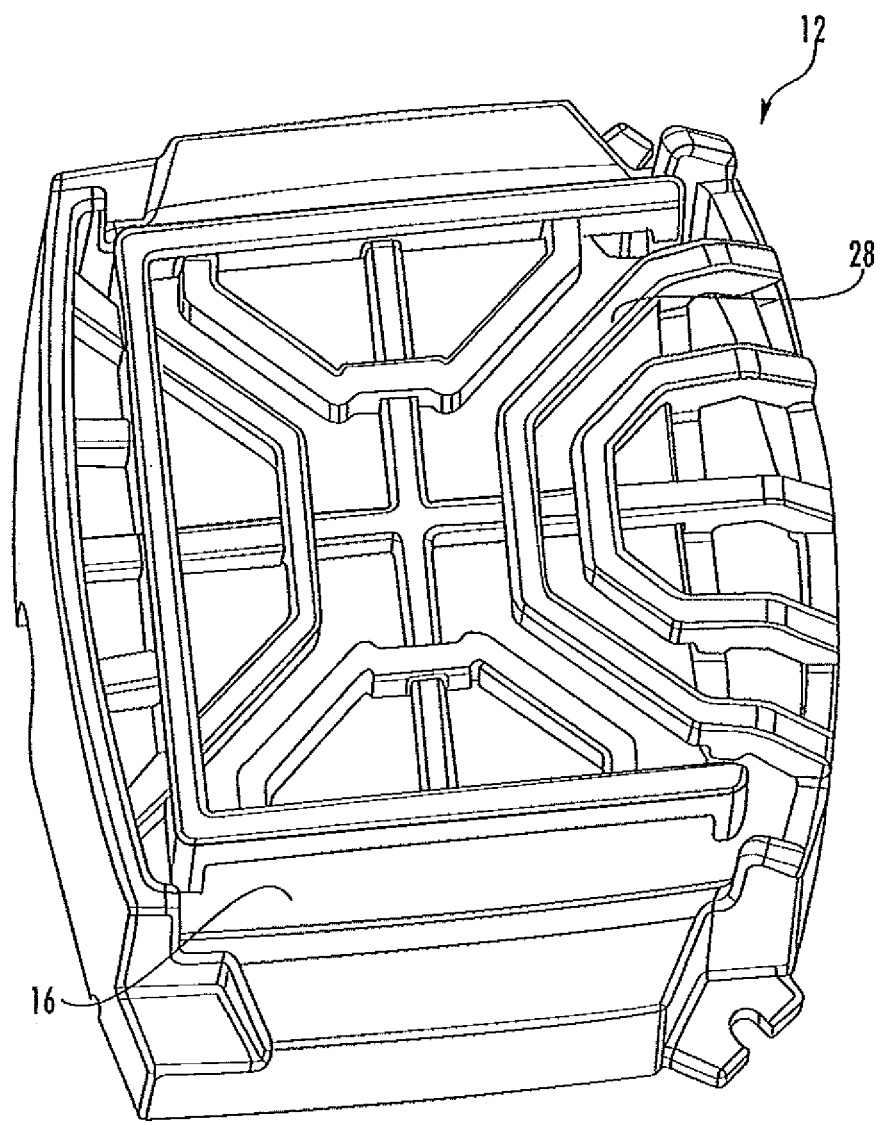
FIG. 2 is top perspective view of the grill showing a first embodiment of the grill pattern.

FIG. 2 is a top perspective view of the grill 12 of this device, under which mat 16 is to be slid. The heater plate 14 may be heated by a flame powered by a butane cartridge located within the body of unit 10 as per the '430 patent. Active liquid ingredient carried on the mat or pad 16 as a volatilized liquid rises from the plate as the active ingredient evaporates when the heater plate 14 is heated. The grill 12 is made of a high temperature nylon which is suitable for the heat from plate 14 and mat 16.

The grill 12 is formed of a pattern of spaced apart ribs 28, forming a plurality of openings shown in the Figures, and the ribs collect condensate as the volatilized liquid active ingredient passes therethrough. The pattern for the ribs enhances dispersion of the active ingredient and keeps the user from touching the mat/pad or plate and also maintaining the mat/pad in place. A first embodiment of a pattern for the grill 12 is seen in FIG. 2 and is substantially rectangular with the ribs forming geometric shapes.

Prior art grills generally are convex in shape being highest in the center of the grill and tapering downwardly and outwardly from the center toward the periphery. Such grill structure directs the condensate formed on the ribs to migrate outwardly towards the outside perimeter 30 of the grill (See FIG. 3). As the condensate migrates towards outer perimeter 30, it drips downwardly onto the device therebelow. The condensate drips onto the mechanical elements below the heater plate, as it drips from the outer periphery of the grill. This may cause the condensate to interfere with the effective operation of the elements below the heating plate. The condensate migrating towards the outer perimeter 30 of grill 12 also constitutes a waste of condensate that could be better used by the device reheating and evaporating the condensate migrating along ribs 28 of this invention.

Figure 3:
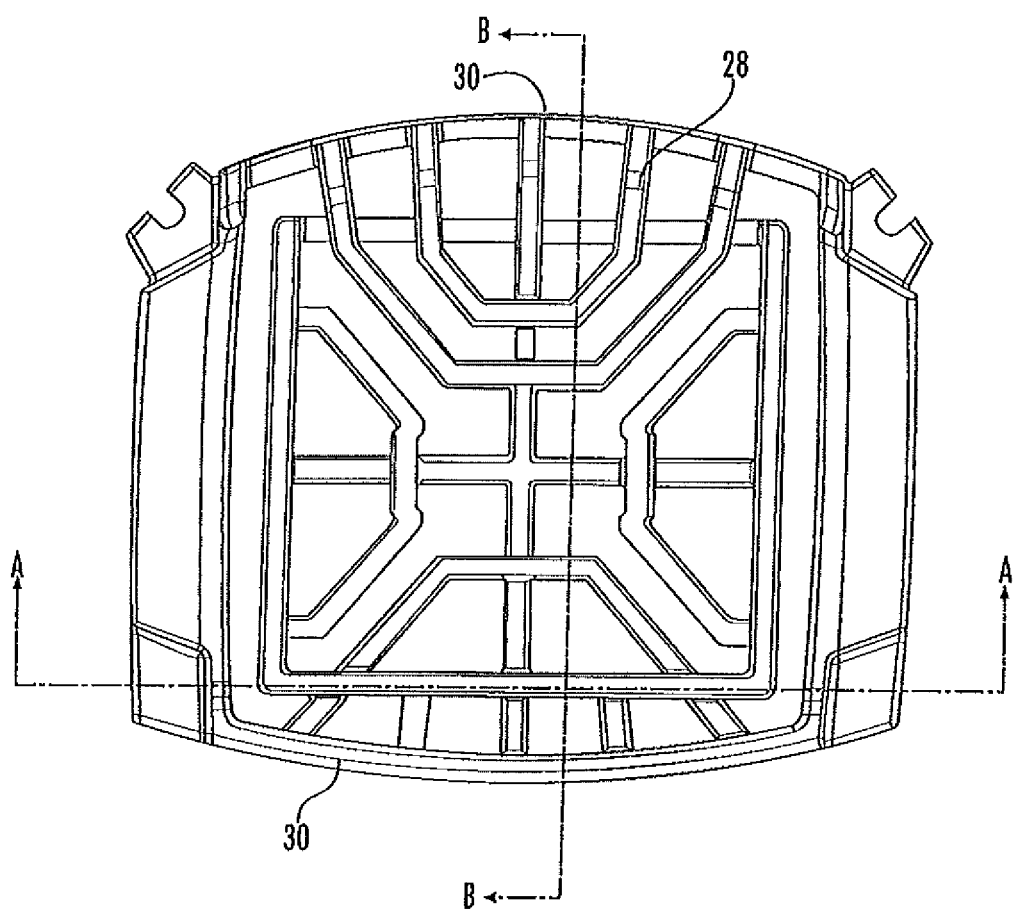
FIG. 3 is a top view of a first embodiment of the grill of this invention with cross-sectional lines A-A and B-B indicated.
Figure 4:
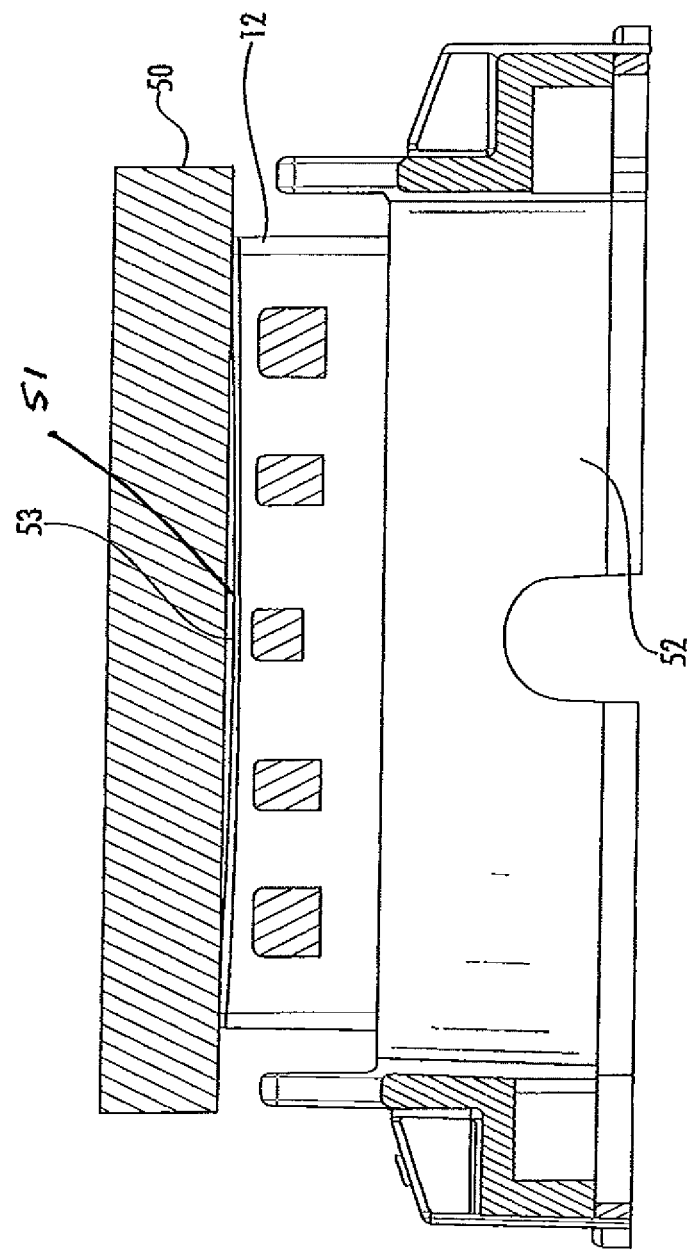
FIGS. 4 and 5 are cross-sectional views along A-A and B-B of FIG. 3, with FIG. 5 having a phantom block for illustrating the concave curvature of the grill and FIG. 5 having the mat on top of the heated plate.
Figure 5:
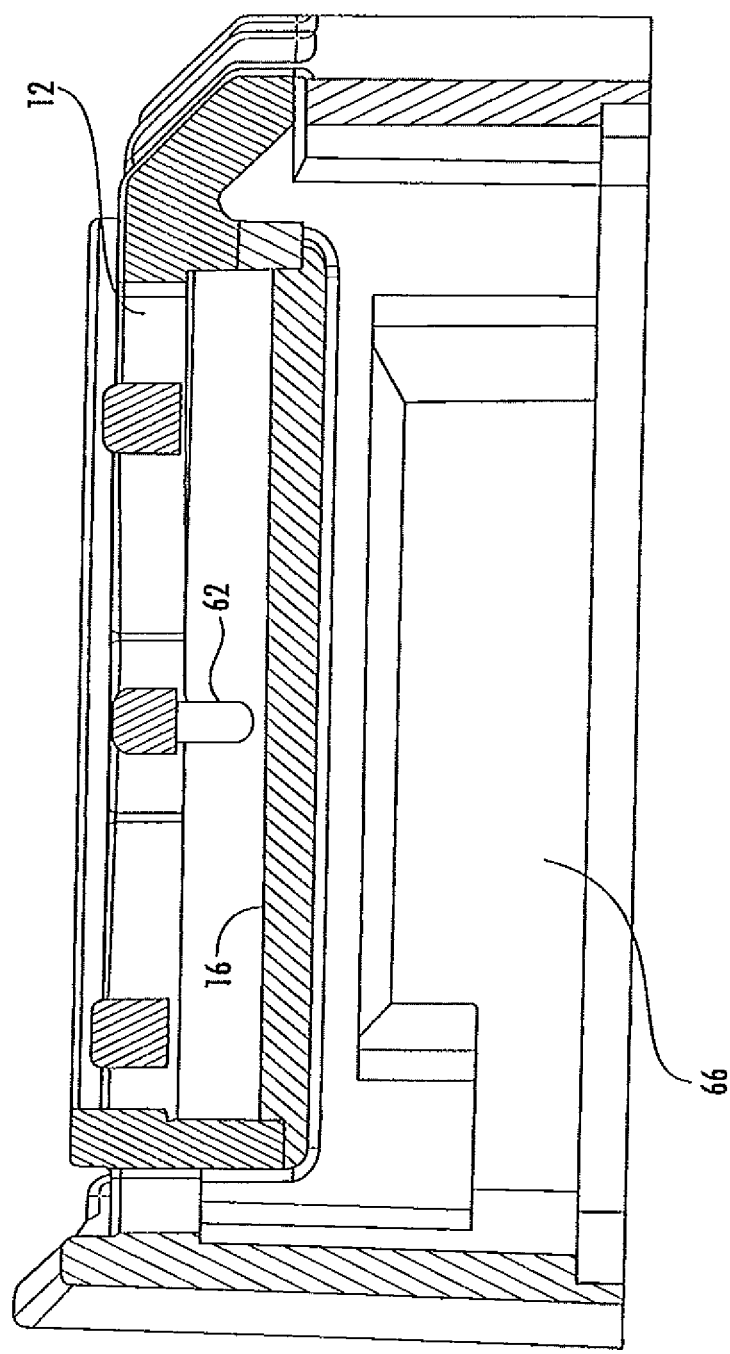
Figure 6A:
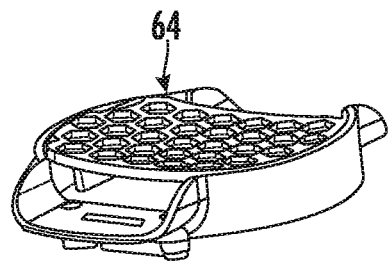
FIGS. 6a, 6b and 6c are perspective, side plan and top plan views, respectively, of another embodiment of the grill of this invention.
Figure 6B:
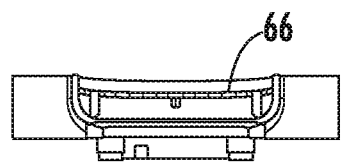
Figure 6C:
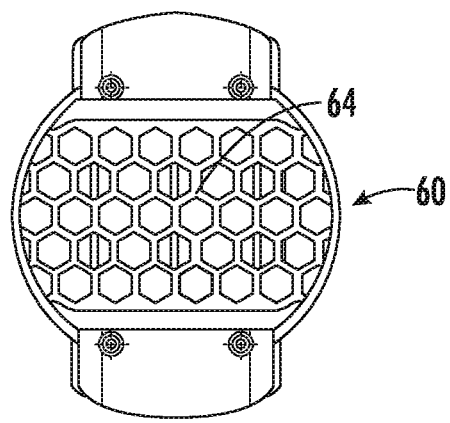
Figure 7A:
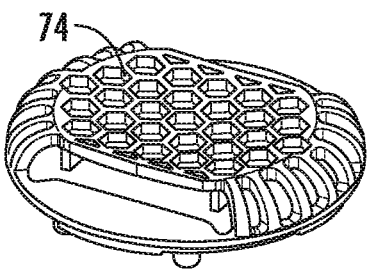
FIGS. 7a, 7b and 7c are perspective, side plan and top plan views, respectively, of still another embodiment of the grill of this invention.
Figure 7B:
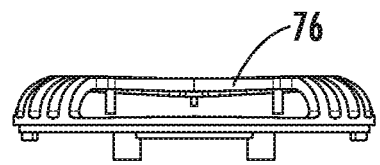
Figure 7C:
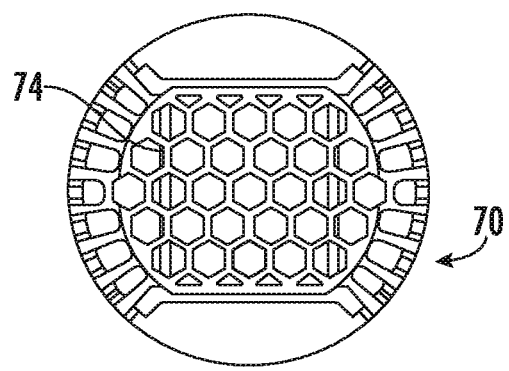

FIGS. 4 and 5 are sectional views taken along lines A-A and B-B of FIG. 3. For purposes of illustrating the slight central curvature of the ribs 28, a theoretical block 50 is shown on top of the grill illustrating a slight separation between the flat bottom of the block 50 and the top of grill 12. As can be seen in FIG. 5, a space 51 is formed between the bottom of block 50 and the top of grill 12. That space 51 is formed by the slight concave curve in the grill 12 with the middle 53 of the grill being the lowest point of the curvature of the ribs. As may be readily understood, with the grill structure of FIG. 3, the condensate tends to migrate towards the center of the grill and moves along the ribs in that direction so as to drip the condensate directly onto the mat and heater therebelow, causing the condensate to be reheated and re-evaporated. FIGS. 4 and 5 show the side walls 52 and 60 of the grill which sits on device 10 above the heated plate 14. FIG. 5 also shows a finger 62 integrally formed under the grill 12 holding the mat in place.

The undersides of the grill ribs have a similar concave curve as the top of the ribs 28, thereby carrying the condensate on the undersides of the ribs toward the center to drip on the mat.

FIGS. 6a, 6b, 6c and 7a, 7b and 7c are views of additional embodiments of the concave grills 60 and 70 of this invention. These grills have different outer shapes for different insect repellent sections 19. Additionally, the grills are formed of a plurality of openings arranged in rows 64 allowing the volatilized liquid to pass upwardly therethrough forming a condensate and causing the condensate to migrate toward the centers of the grills. The concave shapes of the top of the grills 60 and 70 is seen at locations 66 and 76. The embodiment of FIG. 6 shows the grill 60 formed of pairs of opposite sides with one pair being rounded and the other pair being straight. The embodiment of FIG. 7 shows a round shape for the grill 70.

This invention is disclosed with respect to an operating device having a heated plate and a grill thereabove. Since a heated plate will be heating an article containing liquid located on top of the plate which liquid evaporates and rises from that article, condensate will conventionally form on the protective grill thereabove. Other heat generating operating devices causing a heated vapor to rise through a grill can advantageously use this invention.

This invention has been described with respect to a preferred embodiment of an insect repellent device, but its application to protective grills utilizing a heated surface with a mat or some structure thereupon carrying a liquid ingredient to be evaporated applies to other environments in order to both conserve the active ingredient, allowing it to be reused and preventing condensate formed on the grills from causing degradation of the unit therebelow.

The benefits achieved with the concave grill of this invention can be realized for systems other than mats in which liquid is evaporated. For instance, liquid in open bottles, liquid on trays, liquid in gel form, liquid in bottles having wicks also will benefit from this invention. The benefits of this invention can also apply to other larger systems in which a vaporized substance passes through a relatively cool grill.

It should be understood that the preferred embodiment was described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly legally and equitably entitled.

The invention claimed is:

1. A method for retrieving and reusing condensate formed on a grill of an insect repellant device, said grill formed from a plurality of ribs, each rib having an underside, said grill having an outer perimeter and a center, said grill forming a part of said insect repellent device which operates by impregnating a mat with an active ingredient and heating said mat on a heating plate causing said active ingredient to vaporize and rise through said grill and form a condensate of said active ingredient on said grill, said method comprising:

providing said grill with a concave shape with the outer perimeter being higher than the center of said grill, carrying condensate formed on undersides of said ribs inwardly from said outer perimeter toward the center of said grill, dropping said condensate from said grill onto said mat, reusing said condensate dropped from said grill to form vapor by heating said condensate dropped onto said mat.

2. The method according to claim 1, wherein said grill is formed by a plurality of openings allowing said heated vapor to pass therethrough.

3. The method according to claim 1, wherein said plurality of ribs form geometric shapes.

4. The method according to claim 1, wherein said outer perimeter of said grill comprises a round shape.

5. The method according to claim 1, wherein said outer perimeter of said grill is substantially rectangular.

6. The method according to claim 1, wherein a top and an underside of the grill are both concave shaped.

\* \* \* \* \*